United States Patent [19]

Candau et al.

[11] Patent Number: 5,599,800
[45] Date of Patent: Feb. 4, 1997

[54] ORGANOPOLYSILOXANE COMPOSITION OF GEL-LIKE APPEARANCE, CONTAINING NO GELLING AGENT, WHICH MAY BE USED IN COSMETICS AND DERMATOLOGY

[75] Inventors: Didier Candau, Bievres; Pascal Simon, Vitry Sur Seine, both of France

[73] Assignee: L'Oreal, Paris, France

[21] Appl. No.: 317,486

[22] Filed: Oct. 4, 1994

[30] Foreign Application Priority Data

Oct. 4, 1993 [FR] France ................................ 93 11802

[51] Int. Cl.$^6$ .......................... A61K 31/70; A61K 31/715
[52] U.S. Cl. ................. 514/53; 514/54; 514/63; 514/844; 514/846; 514/847; 514/848; 514/873; 514/880; 536/115; 536/123.1; 536/123.13
[58] Field of Search ................. 514/53, 54, 63, 514/844, 846, 847, 848, 873, 880; 536/115, 119, 123.1, 123.13

[56] References Cited

U.S. PATENT DOCUMENTS 4,946,832  8/1990  Goode et al. ........................ 514/53

FOREIGN PATENT DOCUMENTS

| 0559320 | 9/1993 | European Pat. Off. . |
| 61-040204 | 2/1986 | Japan . |
| 63-216817 | 9/1988 | Japan . |
| 02229106 | 9/1990 | Japan . |
| 04300831 | 10/1992 | Japan . |
| 05004911 | 1/1993 | Japan . |
| 05043418 | 2/1993 | Japan . |
| 05139929 | 6/1993 | Japan . |
| 05178734 | 7/1993 | Japan . |
| 9417830 | 8/1994 | WIPO . |
| 9417774 | 8/1994 | WIPO . |

*Primary Examiner*—Gary E. Hollinden
*Assistant Examiner*—Howard C. Lee
*Attorney, Agent, or Firm*—Oblon, Spivak, McClelland, Maier & Neustadt, P.C.

[57] ABSTRACT

Compositions of gel-like appearance, comprising an oily phase formed of at least 75% of organopolysiloxane, dispersed in an aqueous phase containing at least 25% of water, using an emulsifying agent formed of at least one sucrose ester, are stable in the presence of compounds which are not compatible with conventional gelling agents.

15 Claims, No Drawings

ORGANOPOLYSILOXANE COMPOSITION OF GEL-LIKE APPEARANCE, CONTAINING NO GELLING AGENT, WHICH MAY BE USED IN COSMETICS AND DERMATOLOGY

BACKGROUND OF THE INVENTION

1. Field of the Invention

The present invention relates to organopolysiloxane compositions of shiny and gel-like appearance, which contain no gelling agent. The present compositions constitute an excipient of choice for incorporating substances that are incompatible with the gelling agents conventionally used in preparations of gel-like appearance. The present compositions may serve as a base for the manufacture of creams used in many fields, in particular in cosmetology, dermatology, pharmaceutics and the like. The present invention very especially relates to care or makeup creams for the skin, the face and the body in general including the nails, the scalp and the eyelashes.

2. Discussion of the Background

Many products already exist both as cosmetic and dermatological or pharmaceutical products which are oil-in-water (O/W) emulsions. Depending on the choice of the starting materials (emulsifying agents, fatty substances, polyol polymers and other hydrophilic starting materials and the like), these dispersions may be provided in the form of creams of varied textures: more or less thick, more or less shiny and more or less gel-like.

In order to obtain a cream which is pleasant from a sensory (its "feel") and from a visual (its appearance) point of view, the search is more for a shiny and gel-like appearance rather than a runny and matt appearance. In order to obtain such creams, a gelling agent (also known as a thickener) is customarily used, which is incorporated into the continuous aqueous phase of the emulsion and which imparts its consistency to the cream. The majority of the gelling agents conventionally used are carboxyvinyl polymers of the Carbomers (CTFA) type, which are neutralized by a base (sodium hydroxide or triethanolamine).

It happens, however, that certain starting materials, which are moveover indispensable in the composition of these creams, do not permit the use of the above-mentioned gelling agents as a result of incompatibility. It is known, for example, that electrolytes (inorganic and organic salts) are incompatible with neutralized carboxyvinyl polymers because of the fact that they "break" the emulsion or even liquefy it.

A large number of starting materials used in O/W emulsions of gel-like appearance are either electrolytes in their entirety or mixtures of various compounds which may include non-negligible amounts of electrolytes. Thus, formulations containing carboxyvinyl polymers and electrolytes lack consistency, and their appearance renders them inappropriate for use in the above-mentioned fields. This same problem is also encountered with any compound, other than an electrolyte, displaying an incompatibility with these carboxyvinyl gelling agents.

One solution consists of using, in place of the carboxyvinyl polymer gelling agents, gelling agents of the polysaccharide type such as natural gum of cellulose, guar, or xanthan. However, in order to obtain a consistency equivalent to that provided by the gelling agents of carboxyvinyl polymer type, large amounts of such gelling agents must be incorporated in order to increase the viscosity of the emulsion. This is a nuisance in the above-mentioned applications, because the cream of gel-like appearance then becomes very sticky when applied to the skin, the hair, etc.

It is moreover known, according to U.S. Pat. No. 5,013,715, to produce an anhydrous base of pasty and matt appearance in order to prepare cosmetic creams. This base consists of a fluid organopolysiloxane oil of the methylphenylpolysiloxane type, used alone or mixed with a cyclic polydimethylsiloxane (PDMS) and/or a linear PDMS, and of sucrose ester. This ester has a pronounced lipophilic nature, because its hydroxyl number is less than 200, in order to be compatible with the fluid organopolysiloxane. The addition of water to this anhydrous paste leads to the production of a composition which is applied to the skin with difficulty.

It is also known, according to EP-A-158,108, that it is possible to produce O/W emulsions by adding water to anhydrous detergent compositions comprising an oily phase, a detergent emulsifying agent and a sucrose ester. These emulsions are milky creams of low viscosity, which are difficult to apply to the skin and the hair.

The need thus remains for gel-like compositions that do not display the disadvantages encountered with the known preparations, in particular of runny consistency, of instability, of matt appearance, of unpleasant sensation to the touch, of sticky effect, of unsatisfactory spreading and of incompatibility with certain compounds.

SUMMARY OF THE INVENTION

Accordingly, it is one object of the present invention to provide novel gel-like compositions.

It is another object of the present invention to provide gel-like compositions which do not have a runny consistency.

It is another object of the present invention to provide gel-like compositions which are stable.

It is another object of the present invention to provide gel-like compositions which have a shiny appearance.

It is another object of the present invention to provide gel-like compositions which have a pleasant sensation to the touch.

It is another object of the present invention to provide gel-like compositions which are not sticky.

It is another object of the present invention to provide gel-like compositions which exhibit good spreading properties.

It is another object of the present invention to provide gel-like compositions which are compatible with compounds, which are incompatible with conventional gelling agents, such as electrolytes.

These and other objects, which will become apparent during the following detailed description, have been achieved by the inventors' discovery that compositions of gel-like appearance, containing no gelling agent, allow the above-described disadvantages to be overcome. Specifically, the present compositions comprise an oily phase containing at least 75% by weight, based on the total weight of the oily phase, of an organopolysiloxane dispersed in an aqueous phase containing at least 25% by weight, based on the total weight of the aqueous phase, of water, and an emulsifying agent formed exclusively of at least one sucrose ester.

DETAILED DESCRIPTION OF THE PREFERRED EMBODIMENTS

In the present invention, compositions "of gel-like appearance" are understood to include any type of creamy product of a certain consistency, which does not run under its own weight and which has a viscosity greater than or equal to 1 Pa.s.

One advantage of the present oil-in-water compositions is that they allow the introduction of one or more hydrophilic additives having active properties from a cosmetic and/or dermatological and/or pharmaceutical point of view into the aqueous phase, without modifying its gel-like texture.

These hydrophilic active agents are mainly electrolytes. The term "electrolyte" is understood to refer to an organic or inorganic salt of an organic or inorganic acid and of an organic or inorganic base.

The composition of the present invention advantageously comprises, by weight:

from 5% to 50% of oily phase from 1% to 20% of sucrose ester from 30% to 94% of aqueous phase from 0% to 5% of additive, all amounts given in % by weight, based on the total weight of the composition.

Even more preferably, the present composition comprises, by weight:

from 15% to 35% of oily phase from 3% to 8% of sucrose ester from 54% to 81% of aqueous phase from 0% to 5% of additive, all amounts given in % by weight, based on the total weight of the composition.

According to the present invention, the electrolyte or the mixture of electrolytes is present in an amount of 0.01% to 1% by weight, preferably 0.05 to 0.5 % by weight, based on the total weight of the composition.

Surprisingly, the gel-like appearance of the composition of the present invention is not disturbed by the introduction of an electrolyte or of any material which is incompatible with conventional gelling agents of the carboxyvinyl type, for example ammonium and imidazolinium salts and certain preserving agents such as di(4-amidinophenoxy)-1,6-hexane diisethionate.

The hydrophilic active agents such as the electrolytes are chosen from the group comprising hydrating agents, anti UV-A, anti UV-B and anti UV-C filters, keratolytic agents, anti-ageing agents, anti-wrinkle agents, antioxidants, depigmenting agents, liporegulators, antiinflammatories, fresheners, cicatrizing agents, antibacterial agents, antifungal agents, antiperspirants, anti-dandruff agents, permanent-wave reducing agents, hair conditioners, nourishing agents and film-forming agents (restructuring agents, tension agents and plasticizers).

The electrolyte is preferably chosen from sodium salts such as sodium pyrrolidonecarboxylate, which acts as a hydrating agent, the sodium salt of 3,3'-(1,4-phenylenedimethylidyne)bis[7,7-dimethyl-2-oxobicyclo[2.2.1]heptane-1-methanesulphonic] acid, which serves as an anti UV-A sunscreen agent, imidazolinium or magnesium salts, salts of salicylic acid and of derivatives thereof such as those cited in EP-A-378,936, serving as anti-ageing agents, and salts of alpha-hydroxy acids such as those described in U.S. Pat. No. 4,380,549 or in WO 92/18116, which serve for the care of withered skin or for retarding its ageing, such as ammonium salts.

The oily phase comprises at least 75% by weight, preferably at least 90% by weight, based on the total weight of the oily phase, of the organopolysiloxane. According to a preferred aspect of the present invention, the organopolysiloxane is chosen from cyclodimethylsiloxanes such as, for example, cyclopentadimethylsiloxane; polydimethylsiloxanes of varying viscosity such as, for example, DC fluids 200 cSt to 12,500 cSt ($2.10^{-2}$ m$^2$/s to 1.2 m$^2$/s) sold by Dow Corning or Abil 10 sold by Goldschmidt; polyalkoxysiloxanes such as, for example, polystearoxydimethylsiloxane Abil Wax 2434 sold by Goldschmidt; polyalkylsiloxanes such as, for example, polycetylmethylsiloxane Abil Wax 9801 sold by Goldschmidt; polyhydroxysiloxanes such as, for example, Q2-1403 Fluid from Dow Corning; polyphenylsiloxanes such as, for example, the polyphenylmethylsiloxane Silbione 70641 V200 sold by Rhône-Poulenc or the polyphenyltrimethylsiloxane Abil AV 20 from Goldschmidt.

The alkyl or alkoxy group of the organopolysiloxanes generally contains from 12 to 22 carbon atoms.

The remainder of the oily phase contains any type of inorganic, organic, vegetable or synthetic oil. The oils used are those known by a person skilled in the art, such as karite butter (see U.S. Pat. No. 4,661,343), almond oil, apricot oil, synthetic perhydrosqualene and esters of fatty acids and of $C_1$ to $C_{30}$ alcohols such as 2-ethylhexyl palmitate and isopropyl myristate.

The aqueous phase comprises at least 25% by weight, preferably at least 50% by weight, based on the total weight of the aqueous phase, of water.

According to another preferred aspect of the invention, the sucrose ester is chosen from the group comprising esters of saturated or unsaturated, linear or branched $C_7$ to $C_{22}$, preferably $C_{12}$ to $C_{22}$, fatty acids and sucrose, the fatty acids being, for example, attached to the sucrose unit in position C2 and/or C3 and/or C5 and/or C6 of the fructose residue and/or in position C2 and/or C3 and/or C4 and/or C6 of the glucose residue.

These esters will preferably by chosen from the mono-, di-, tri- and tetraesters and polyesters comprising monoesters in an amount of 30% to 95% by weight relative to the total weight of ester.

The sucrose ester advantageously has a hydroxyl number which imparts a pronounced hydrophilic nature thereto.

The sucrose esters in accordance with the invention are, for example, those sold by the company Crodesta under the names F160, F140, F110, F90, F70 and SL40, respectively denoting the sucrose palmitostearates formed of 73% monoester and 27% di- and triester; of 61% monoester and 39% di-, tri-, and tetraester; of 52% monoester and 48% di-, tri-, and tetraester; of 45% monoester and of 55% di-, tri-, and tetraester; of 39% monoester and of 61% of di-, tri-, and tetraester; and sucrose monolaurate. It is also possible to mix these various products in various percentages in order to obtain the desired consistency.

It is also possible to use the sucrose esters sold by the company Mitsubishi under the name Ryoto sugar esters, for example under the reference B370, and corresponding to sucrose behenate formed of 20% monoester and 80% di-, tri-, and polyester. This compound is preferably combined with the above-mentioned sucrose esters.

The compositions according to the present invention may also comprise one or more additives other than an electrolyte. Such additives may be chosen from the group comprising agents which are well known to a person skilled in the art, for example, co-emulsifying agents such as $C_{12}$ to $C_{22}$ fatty alcohols or mono- or diglycerides, emulsion stabilizing agents such as polysaccharide polymers, in low dose (0.1% to 0.3%), antioxidants (vitamins or esters thereof), preserving agents, dyes, pigments, fragrances, hydrating agents such as polyols (glycerine or sorbitol) and glycols (butylene or hexylene glycol), amino acids and derivatives thereof and the like.

These additives are used at the concentrations commonly accepted for each of them, in particular depending on its degree of solubility. The additives cited may generally be used in an amount of 0.05% to 5% by weight, preferably, 0.1 to 2% by weight, based on the total weight of the composition.

According to a particularly preferred aspect of the present invention, the composition of gel-like appearance containing no gelling agent consists of, by weight:

from 5% to 50% of an oily phase, comprising of at least 75% of organopolysiloxane, dispersed in an aqueous phase;

from 1% to 20% of sucrose ester serving as an emulsifying agent;

from 30% to 93.9% of aqueous phase; and from 0.1% to 1% of an electrolyte formed of the sodium salt of 3,3'-(1,4-phenylenedimethylidyne)bis[7,7-dimethyl-2-oxobicyclo[2.2.1]heptane-1-methanesulphonic] acid.

The present compositions may be prepared by conventional methods. For example, the sucrose ester may first be dissolved in the aqueous phase with heating and stirring. The aqueous phase may then be introduced into the oily phase, which has been heated beforehand, with rigorous stirring to give the final emulsion.

The present method also provides methods for treating the skin, hair, nails, scalp, and/or eyelashes by topical application of the present composition. As noted above, the present composition have a good feel to the touch, are not sticky, and spread easily. Thus, the present invention relates to a use of the composition described above for the cosmetic treatment of the skin, the nails, the scalp and the eyelashes. The present invention also relates to the use of the present composition in order to obtain a cream which is intended for the dermatological treatment of the skin and of the scalp.

As noted above, the present compositions may contain compounds which are not compatible with conventional gelling agents. This is possible, because the present compositions do not contain a conventional gelling agent such as a carboxyvinyl polymer or a polysaccharide gelling agent such as a natural gum of cellulose, guar, or xanthan.

The gelling agents which are not present in the present compositions included hydrophilic gelling agents such as water-soluble or colloidally water-soluble polymers, and include cellulose ethers (e.g. hydroxyethyl cellulose, methyl cellulose, hydroxypropylmethyl cellulose), polyvinylpyrrolidone, polyvinylalcohol, guar gum, hydroxypropyl guar gum and xanthan gum. In particular, the gelling agents excluded from the present composition included acrylic acid/ethyl acrylate copolymers and the carboxyvinyl polymers sold by the B.F. Goodrich Company under the trade mark of Carbopol resins. These resins consist essentially of a colloidally water-soluble polyalkenyl polyether crosslinked polymer of acrylic acid crosslinked with from 0.75% to 2.00% of a crosslinking agent such as for example polyallyl sucrose or polyallyl pentaerythritol. Examples include Carbopol 934, Carbopol 940, Carbopol 950, Carbopol 980, Carbopol 951 and Carbopol 981, Carbopol 934 is a water-soluble polymer of acrylic acid cross-linked with about 1% of a polyallyl ether of sucrose having an average of about 5.8 allyl groups for each sucrose molecule. Also excluded are hydrophobically-modified cross-linked polymers of acrylic having amphipathic properties available under the Trade Name Carbopol 1382, Carbopol 1342 and Pemulen TR-1 (CTFA Designation: Acrylates/10–30 Alkyl Acrylate Crosspolymer). Combinations of the polyalkenyl polyether cross-linked acrylic acid polymer and the hydrophobically modified cross-linked acrylic acid polymer are also excluded.

Other features of the invention will become apparent in the course of the following descriptions of exemplary embodiments which are given for illustration of the invention and are not intended to be limiting thereof.

EXAMPLES

In the following examples, the following experimental procedure is used: the sucrose ester is first of all incorporated into water possibly containing hydrophilic additives (for example electrolytes), followed by heating between 60° C. and 70° C. with moderate stirring for 15 to 45 minutes. When the ester is fully dissolved, the emulsion is produced by introduction into the aqueous phase of the oily phase which has been heated beforehand to 60° C. and which possibly contains lipophilic additives, followed by vigorous stirring by shearing using a "Moritz" type mixer for 5 to 15 minutes, while maintaining the heating. Finally, it is allowed to return to room temperature with moderate stirring (using a mixer with blades) in order to degas the emulsion.

The result is a cream of shiny and gel-like appearance with a viscosity greater than 1 Pa.s.

The compositions below are given in percentage by weight, based on the total weight of the composition.

Example 1

| | |
|---|---|
| Sucrose palmitostearate CRODESTA F70 (45% monoester, 55% di-triester) | 6 |
| Behenyl alcohol (co-emulsifying agent) | 2.5 |
| Polydimethylsiloxane (Dow Corning Fluid 200 - 10 cSt) | 25 |
| BHA, BHT (antioxidants) | 0.8 |
| Methyl para-hydroxybenzoate (preserving agent) | 0.4 |
| Water | qs 100 |

The oil-free cream obtained is non-sticky, pleasant and intended for skin types which tend to be greasy.

Example 2

| | |
|---|---|
| Sucrose palmitostearate CRODESTA F70 (45% monoester, 55% di-triester) | 8 |
| Polydimethylsiloxane (Dow Corning Fluid 200–200 cSt) | 7 |
| Cyclopentadimethylsiloxane (Dow Corning Fluid 245) | 5 |
| Polystearoxydimethylsiloxane (Abil Wax 2434 - Goldschmidt) | 3 |
| Liquid karite butter (oil) | 3 |
| BHA, BHT | 0.4 |
| Imidazolidinyl urea (preserving agent) | 0.05 |
| Water | qs 100 |

The cream obtained is shinny and gel-like, easy to apply to the skin and serves for the care of dry skin-types.

Example 3

| | |
|---|---|
| Sucrose palmitostearate CRODESTA F50 (20% monoester, 80% di-tri-polyester) | 4 |
| Sucrose laurate SL 40 CRODESTA | 4 |
| Cetyl alcohol (co-emulsifying agent) | 0.5 |
| 13% polydimethylsiloxanol-87% polydimethylsiloxane 5 cSt (Dow Corning Q2-1403 Fluid) | 4 |
| Polyphenylmethylsiloxane | 15 |

-continued

| | |
|---|---|
| (Silbione 70641 V200-Rhone Poulenc) | |
| Cyclopentadimethylsiloxane | 20 |
| BHA, BHT | 0.2 |
| Methyl para-hydroxybenzoate | 0.1 |
| Water | qs 100 |

This cream, of shiny and gel-like appearance, serves for the care of dry skin-types.

EXAMPLE 4

| | |
|---|---|
| Sucrose behenate (Mitsubishi Ryoto sugar esters B370) (20% monoester, 80% di-,tri-, and polyester) | 2 |
| Sucrose palmitostearate CRODESTA F160 (73% monoester, 27% di-triester) | 2.5 |
| 67% polydimethylsiloxane-33% tri-methylsiloxysilicate (Dow Corning Fluid 200–100 cSt) | 3 |
| Polydimethylsiloxane (Dow Corning Fluid 200–100 cSt) | 10 |
| 2-Ethylhexyl palmitate (oil) | 5 |
| Hydroxypropylammonium guar chloride (stabilizing agent) | 0.1 |
| BHA, BHT | 0.4 |
| Imidazolidinyl urea | 0.25 |
| Water | qs 100 |

Example 5

An electrolyte formed of sodium pyrrolidonecarboxylate at a content of 1% by weight relative to the total composition is added to the composition of Example 1. A cream of gel-like appearance is obtained, which is intended for moisturizing the skin.

Comparative Example

NaCl or the electrolyte of Example 5 is added, in the same proportions, to an aqueous gel containing 0.5% of the carboxyvinyl polymer known as "Carbopol" sold by the company Goodrich, neutralized with sodium hydroxide. It is observed that the composition is entirely fluidized and has a viscosity close to that of water. As a result, it no longer corresponds to that which is sought.

Example 6

0.7% of an anti-UVA filter, which is the sodium salt of 3,3'-(1,4-phenylenedimethylidyne)bis[7,7-dimethyl-2-oxo-bicyclo[2.2.1]heptane-1-methanesulphonic) acid, is added to the composition of Example 1.

A sun-protection cream of shiny and gel-like appearance is thus produced.

Example 7

The preserving agent used in the composition according to Example 2 is replaced by di(4-amidinophenoxy)-1,6-hexane diisethionate. The appearance of the cream remains unchanged.

This application is based on French patent application 93-11802, filed on Oct. 4, 1993, which is incorporated herein by reference in its entirety.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A composition, comprising (a) an oily phase comprising at least 75% by weight of organopolysiloxane, dispersed in (b) an aqueous phase comprising at least 25% by weight of water, and (c) an emulsifying agent which is at least one sucrose ester, wherein said composition does not run under its own weight and has a viscosity greater than or equal to 1 Pa.s and wherein said composition contains no gelling agent.

2. The composition of claim 1, wherein said sucrose ester is selected from the group consisting of esters of saturated or unsaturated, linear or branched $C_7$ to $C_{22}$ fatty acids and sucrose.

3. The composition of claim 1, wherein said sucrose ester is selected from the group consisting of esters of saturated or unsaturated, linear or branched $C_{12}$ to $C_{22}$ fatty acids and sucrose.

4. The composition of claim 1, wherein said sucrose ester is a mixture of mono-, di-, tri-, and tetraesters and polyesters and said mixture comprises a monoester in an amount of 30% to 95% by weight, based on the total weight of said sucrose ester.

5. The composition of claim 1, further comprising an electrolyte.

6. The composition of claim 1, wherein said electrolyte is selected from the group consisting of sodium pyrrolidonecarboxylate, the sodium salt of 3,3'-(1,4-phenylenedimethylidyne)bis[7,7-dimethyl-2-oxobicyclo[2.2.1]heptane-1-methanesulphonic] acid, salts of salicylic acid and derivatives thereof, and alpha-hydroxy acid salts.

7. The composition of claim 1, wherein said organopolysiloxane is selected from the group consisting of cyclodimethylsiloxanes, polydimethylsiloxanes, polyalkoxysiloxanes, polyalkylsiloxanes, polyhydroxysiloxanes, and polyphenylsiloxanes.

8. The composition of claim 1, further comprising at least one additive other than an electrolyte.

9. The composition of claim 8, wherein said additive other than an electrolyte is selected from the group consisting of coemulsifying agents, stabilizing agents, antioxidants, preserving agents, dyes, pigments, and fragrances.

10. The composition of claim 1, comprising, by weight, based on the total weight of said composition:
   from 5% to 50% of oily phase;
   from 1% to 20% of sucrose ester;
   from 30% to 94% of aqueous phase; and
   from 0% to 5% of additive.

11. The composition of claim 1, comprising, by weight, based on the total weight of said composition:
   from 15% to 35% of aqueous phase;
   from 3% to 8% of sucrose ester;
   from 54% to 81% of aqueous phase; and
   from 0% to 5% of additive.

12. The composition of claim 5, wherein said electrolyte is present in an amount of 0.01% to 1% by weight, based on the total weight of said composition.

13. The composition of claim 8, wherein said additive is a polysaccharide of natural origin and is present in an amount ranging from 0.1% to 0.3% by weight based on the total weight of said composition.

14. A composition, consisting essentially of by weight, based on the total weight of said composition:
   (a) from 5% to 50% of an oily phase, comprising at least 75% of organopolysiloxane;

(b) from 1% to 20% of sucrose ester serving as an emulsifying agent;

(c) from 30% to 93.9% of aqueous phase; and (d) from 0.1% to 1% of the sodium salt of 3,3'-(1,4-phenylenedimethylidyne)bis[7,8-dimethyl-2-oxobicyclo[2.2.1]heptane-1-methanesulphonic] acid, wherein said oily phase (a) is dispersed in said aqueous phase (c), wherein said composition does not run under its own weight and has a viscosity greater than or equal to 1 Pa.s.

15. A cosmetic or dermatological method of treating the skin, hair, nails, scalp, or eyelashes, comprising topically applying a composition, said composition comprising (a) an oily phase comprising at least 75% by weight of organopolysiloxane, dispersed in (b) an aqueous phase comprising at least 25% by weight of water, and (c) an emulsifying agent which is at least one sucrose ester, wherein said composition does not run under its own weight and has a viscosity greater than or equal to 1 Pa.s and wherein said composition contains no gelling agent.

* * * * *

UNITED STATES PATENT AND TRADEMARK OFFICE
CERTIFICATE OF CORRECTION

PATENT NO. : 5,599,800
DATED : FEBRUARY 4, 1997
INVENTOR(S) : DIDIER CANDAU, ET AL.

It is certified that error appears in the above-identified patent and that said Letters Patent is hereby corrected as shown below:

Column 4, line 32, "will preferably by"

should read --will preferably be--.

Signed and Sealed this

Seventh Day of April, 1998

Attest:

BRUCE LEHMAN

Attesting Officer

Commissioner of Patents and Trademarks